United States Patent [19]
Nishii et al.

[11] Patent Number: 5,498,447
[45] Date of Patent: Mar. 12, 1996

[54] COATING METHOD

[75] Inventors: Hiroyuki Nishii; Masaru Kobayashi, both of Takatsuki; Kazutoshi Toya, Nagaokakyo; Nobuo Uchiyama, Toyonaka, all of Japan

[73] Assignee: Sumitomo Pharmaceuticals Company, Limited, Osaka, Japan

[21] Appl. No.: 331,482

[22] PCT Filed: Apr. 27, 1993

[86] PCT No.: PCT/JP93/00543

§ 371 Date: Nov. 4, 1994

§ 102(e) Date: Nov. 4, 1994

[87] PCT Pub. No.: WO93/21893

PCT Pub. Date: Nov. 11, 1993

[30]    Foreign Application Priority Data

May 7, 1992   [JP]   Japan ................... 4-143362

[51] Int. Cl.$^6$ ....................................... B05D 7/00
[52] U.S. Cl. .................... 437/213; 427/220; 118/303
[58] Field of Search ......................... 427/213, 220; 239/419, 419.3; 118/303

[56]            References Cited
              PUBLICATIONS

Jozwiakowski et al., "Characterization of a Hot–Melt Fluid Bed Coating Process for Fine Granules", Pharmaceutical Research, vol. 7, No. 11, 1990 pp. 1119–1126 (no month).

*Primary Examiner*—Shrive Beck
*Assistant Examiner*—David Maiorana
*Attorney, Agent, or Firm*—Birch, Stewart, Kolasch & Birch

[57]            ABSTRACT

A coating method which is characterized in that, when the surfaces of solid particles kept flowing are spray-coated with a thermally melted wax, a two-fluid nozzle adapted to mix a thermally melted wax with a heating gas in and eject the resultant mixture from one flow passage and eject a heating gas from the other flow passage is used, the two-fluid nozzle having spray ports of a diameter of 1.5 to 5.8 mm, and the two-fluid nozzle having no needle valve. According to this method, the use of an organic solvent for melting wax is omitted, and complicated operations for pulverizing a wax and for thermally melting the wax powder after it has been deposed on solid particles are not required. This method can also prevents clogging of the nozzle, powdering of the melted wax and forming of agglomerated solid, and permits simple and easy production of sustained release preparations and preparations for masking materials of unpleasant and bitter tastes.

9 Claims, 1 Drawing Sheet

COATING METHOD

TECHNICAL BACKGROUND

The present invention relates to a coating method of a wax on the solid particles, More particularly, the present invention relates to a coating method which can make it available a simple and easy spray-coating of a thermally melted wax on the surfaces of solid particles kept flowing without using any organic solvent.

PRIOR ART

There have been well known some methods for preparing sustained release preparations which control the release of an active ingredient therefrom, or preparations for masking materials of unpleasant and bitter tastes, which comprise coating a wax on the surfaces of solid particles containing an active ingredient.

For example, there are disclosed a method of coating solid particles containing an active ingredient with a wax, which comprises dissolving a wax in an organic solvent and spraying the resultant solution on the surfaces of solid particles containing an active ingredient, and drying them (Japanese Patent Second Publication (Kokoku) No. 26837/1965), a method of coating solid particles containing an active ingredient with a wax, which comprises pulverizing a wax to fine powder, depositing said fine powder on the surfaces of solid particles containing an active ingredient, further thermally melting thereof (Japanese Patent Second Publication (Kokoku) No. 3789/1965), and the like. Recently, it has been tried to effect the coating by thermally melting a wax and directly spraying the resultant (cf. PHARM TECH JAPAN, 7, 711–718 ( 1991)).

However, in the coating method which comprises dissolving a wax in an organic solvent and spraying the resultant solution, there are used as an organic solvent, for example, halogenated hydrocarbons such as carbon tetrachloride, chloroform. trichloroethane, etc., hydrocarbons such as hexane, benzene, etc., lower alcohols such as methanol, ethanol, propanol, etc., ketones such as acetone, methyl ethyl ketone, etc., and the use of these solvents has many problems, for example, bad effects on human beings, air pollution, and causes of disasters, etc. Besides, in order to avoid these problems, the method should be carried out in a closed system, and needs a large equipment such as an equipment for recovering organic solvents. Moreover, it has some problems in view of industrial efficiency, because the large amount of organic solvents are used and hence, it takes a lot of time to remove these solvents from the resulting preparations after coating.

In the method which comprises pulverizing a wax to fine powder, depositing said fine powder on solid particles and then thermally melting thereof, the process of pulverization of a wax to fine powder is very complicated, and it should be usually carried out after cooling the wax with liquid nitrogen or dry ice so that a special equipment is needed therefor, and it is difficult to control the size of the powder thus obtained. Further, in this method, it is essential to thermally melt the fine powder alter depositing on the solid particles, and if the temperature of thermal melting is not high enough to melt the wax, the resulting coating is not sufficiently uniform. On the contrary, if the temperature of thermal melting is too high, the wax fuses to cause forming of agglomerated solid particles. Besides, the temperature range at which a wax starts melting and completes melting is usually wide, and hence, it is very difficult to melt the wax at the optimum temperature thereof.

On the other hand, these problems can be solved in the method comprising directly spray-coating a thermally melted wax onto solid particles containing an active ingredient. However, this method includes other problems, for example, clogging of spray nozzle caused by cooling of the thermally melted wax when spraying, powdering of the melted wax caused by finely dividing of spray mist, or forming of agglomerated solid particles caused by coarse particles of spray mist, and hence, it can still not achieve the sufficient coating. That is, in the conventional method, the thermally melted wax is sprayed from the central port of the nozzle having a needle valve by ejecting a heating gas from around the top of the nozzle as well as from outside of the nozzle, in which said nozzle usually has a diameter of below 1.5 mm, and hence, the above-mentioned various problems are induced.

DISCLOSURE OF INVENTION

The present invention provides a coating method of a wax without the above-mentioned problems of the conventional coating methods.

That is, the present invention provides a method for preparing simply and easily sustained release preparations, or preparations for masking materials of unpleasant and bitter tastes, without using any organic solvent for dissolving a wax, or without necessity of complicated operations for pulverizing a wax and for thermally melting the fine powder deposited on solid particles, and further without clogging of the nozzle, powdering of melted wax, and forming of agglomerated solid particles.

The coating method of the present invention comprising spray-coating the surfaces of solid particles kept flowing with a thermally melted wax is characterized in use of a two-fluid nozzle wherein a thermally melting wax and a heating gas are mixed and the resultant mixture is ejected from one fluid passage, and simultaneously the heating gas is ejected from the other fluid passage, and the diameter of spray ports of said two-fluid nozzle being in a range of 1.5 to 5.8 mm, and said two-fluid nozzle having no needle valve.

The present invention cannot be achieved by using the conventional two-fluid nozzle, but can be done by using a two-fluid nozzle having no needle valve with spray ports of a large diameter, and by the inner mixing and outer mixing system of a liquid and a gas.

The solid particles used in the present invention may be prepared from a conventional carrier used in the preparation of solid preparations, for example, fillers such as corn starch, potato starch, lactose, sucrose, mannitol, talc, kaolin, calcium sulfate, calcium carbonate, etc.; lubricants such as magnesium stearate, calcium stearate, etc.; disintegrants such as carboxymethyl cellulose calcium, low-substituted hydroxypropyl cellulose, crystalline cellulose, etc.; binders such as hydroxypropyl cellulose, hydroxypropylmethyl cellulose, polyvinylpyrrolidone, gelatin, polyvinyl alcohol, etc.; or materials used in feed or fertilizer, but should not be limited thereto. In order to incorporate a medicament into the solid particles, a medicament or a mixture of medicament and the above-mentioned carrier is sprayed onto the solid particles thus prepared from a carrier, or a medicament is mixed with a carrier when preparing the solid particles from the carrier. The solid particles may be prepared in the form of either granules, fine granules, pellets or particles, and in the range of 200 to 5000 micron, preferably in the range or 300 to 3000 micron. The crystals of the medicament per se are also available for solid particles of the present invention if the size thereof is within the above-mentioned range. The medicament contained in the solid particles may be any ones which are required to be released gradually, or have unpleasant or bitters tastes, or food, feed, fertilizer, or insecticides, etc., more specifically, for example, drugs such as anti-inflammatory agents, antihistaminics, cardiovascular agents, tranquilizers, antibiotics (e.g. indomethacin, ibuprofen, acetaminophen, caffeine, isopropylantipyrine, carbetapentane citrate, phenylpopanolamine hydrochloride, chloropheniramine maleate, diphenylpyraline hydrochloride, sulpiride, cimetidine, isothipendyl hydrochloride, propranolol hydrochloride, cephalexin, bencyclane fumarate, lithium carbonate, etc.), insecticides (e.g. allethrin, fenitrothion, phenothrin, etc.), feed additives (e.g. biotin, carotin, methionine, etc.), or chemical fertilizers (e.g. urea, phosphoric acid, etc.).

The wax used in the present invention may be any ones which are used in the pharmaceutical preparations, and are solid at ordinary temperature and suitable for the desired sustained release preparation and for masking materials of unpleasant and bitter tastes. The suitable examples of the wax are higher alcohols (e.g. cetyl alcohol, stearyl alcohol, myristyl alcohol, etc.), higher fatty acids (e.g. myristic acid, palmitic acid, stearic acid, behenic acid, etc.), or glycerin esters of these higher fatty acids, i.e. higher fatty acid glycerin esters such as monoglyceride, diglyceride, triglyceride, polyglyceride, fats and oils (e.g. hydrogenated soybean oil, hydrogenated castor oil, Japan wax, hydrogenated beef tallow, etc.), waxes (e.g. carnauba wax, candelilla wax, bees wax, etc.), higher hydrocarbons (e.g. paraffin, ceresin, microcrystalline wax, etc.), or a mixture of these waxes.

The amount of wax coated onto the solid particles is not strictly specified, and should be suitable for the desired sustained release preparations or for masking materials of unpleasant and bitter tastes, and can vary in accordance with the kinds of medicaments used therein, the form and the size of the solid particles containing said medicament, the kinds of the coating apparatus used therein, the conditions of spraying a thermally melted wax and a heating gas, or the kinds of wax, but it is usually in the range of 1 to 60 parts by weight, preferably 3 to 40 parts by weight, to 100 parts by weight of the solid particles, so that the surfaces of solid particles are uniformly coated with a thermally melted wax.

The solid particles may be prepared by a conventional method, for example, extrusion, milling granulation, fluidized bed granulation, rolling-granulation, high-shear mixing granulation, etc., but in order to make the more uniform coating, it is preferable to use solid particles having smooth surfaces.

In order to keep the solid particles flowing, there is used an apparatus such as a fluidized bed granulator, a centrifugal granulator, a conventional coating pan, a side vented coating pan, a vacuum coating pan, a high-shear mixer or a combination of these apparatuses, and the apparatus should be selected in accordance with the kinds of thermally melted wax, and the form and size of solid particles to be coated, etc., but it is preferably a centrifugal granulator or a high-shear mixer which shows a strong force to flow.

The method of the present invention is carried out by using a two-fluid nozzle wherein a thermally melting wax and a heating gas are mixed and the resultant mixture is ejected from one flow passage, when the surfaces of solid particles kept flowing are spray-coated with a thermally melted wax, and simultaneously said heating gas is ejected from the other flow passage, and the diameter of spray ports of said two-fluid nozzle being in a range of 1.5 to 5.8 mm, and said two-fluid nozzle having no needle valve. That is, the present invention cannot be achieved by using a conventional two-fluid nozzle used in this field, but by using a two-fluid nozzle having no needle valve with spray ports of a large diameter, and by the inner and outer mixing system of a liquid and a gas. Said two-fluid nozzle preferably has spray ports of a diameter of 1.5 to 5.8 mm, preferably 2 to 4 mm, in order to prevent the problems such as the clogging of the nozzle caused by cooling of melted wax, the powdering of melted wax, and the forming of agglomerated solid particles. Besides, said two-fluid nozzle does not have needle valve. As a suitable example of said two-fluid nozzle, there are Atomax® CNP, CN nozzle (manufactured by Seito Kyoritsu Syokai), etc. wherein a thermally melted wax and a heating gas are mixed, and the resultant mixture is ejected from the top thereof, simultaneously a heating gas is ejected from the top of the nozzle.

It is necessary to heat and keep the thermally melted wax at a temperature over the melting point of wax until it is ejected from said two-fluid nozzle, and the thermally melted wax is transported into said two-fluid nozzle by a pump or a pressure tank, or by self-suction of the nozzle. The mixture of a thermally melted wax and a heating gas is sprayed at a temperature of 1° to 100° C. higher, preferably 5° to 70° C. higher, than a melting point of the wax at the surfaces of the solid particles to be coated, and the temperature thereof may be determined in accordance with the kinds of wax to be used, the kinds and forms of solid particles to be coated, or an apparatus to be used.

The temperature of spraying the thermally melted wax and the heating gas is controlled by heating the wax to be thermally melted at a temperature of 1° to 50° C. higher than the melting point of the wax, and by heating the heating gas at 100° to 800° C., so that the temperature of the mixture of the thermally melted wax and the heating gas is in the above-mentioned temperature range at the surfaces of solid particles, and it is preferably controlled by adjusting the temperature of heating gas, or moreover, by adjusting the distance between the two-fluid nozzle from which the thermally melted wax and the heating gas are ejected, and the surfaces of the solid particles to be coated, in the range of 1 to 30 cm.

The pressure of the heating gas may vary in accordance with the kinds of wax to be used, heating temperature of melted wax, or temperature of heating gas, etc., and may be controlled so that the thermally melted wax can be well ejected, but it is usually in the range of 0.05 to 10 kg/cm$^2$, preferably in the range of 0.1 to 5 kg/cm$^2$. The heating gas includes, for example, air, nitrogen gas, carbon dioxide, steam, or a mixture thereof, but it may be any one which is gaseous at ordinary temperature.

The rate of spraying the thermally melted wax and the heating gas varies in accordance with the forms and the size of solid particles, the amount of the materials, the kinds of the apparatus for coating, the conditions for spraying the thermally melting wax and the heating gas, or the kinds of the wax, but it is usually in the range of 0.5 to 100 ml/min., preferably in the range of 1 to 50 ml/min., per one two-fluid nozzle for ejecting the thermally melted wax and the heating gas so that the surfaces of the solid particles are uniformly coated with the thermally melted wax without the forming of agglomerated solid particles.

BEST MODE FOR CARRYING OUT THE INVENTION

Figure 1:
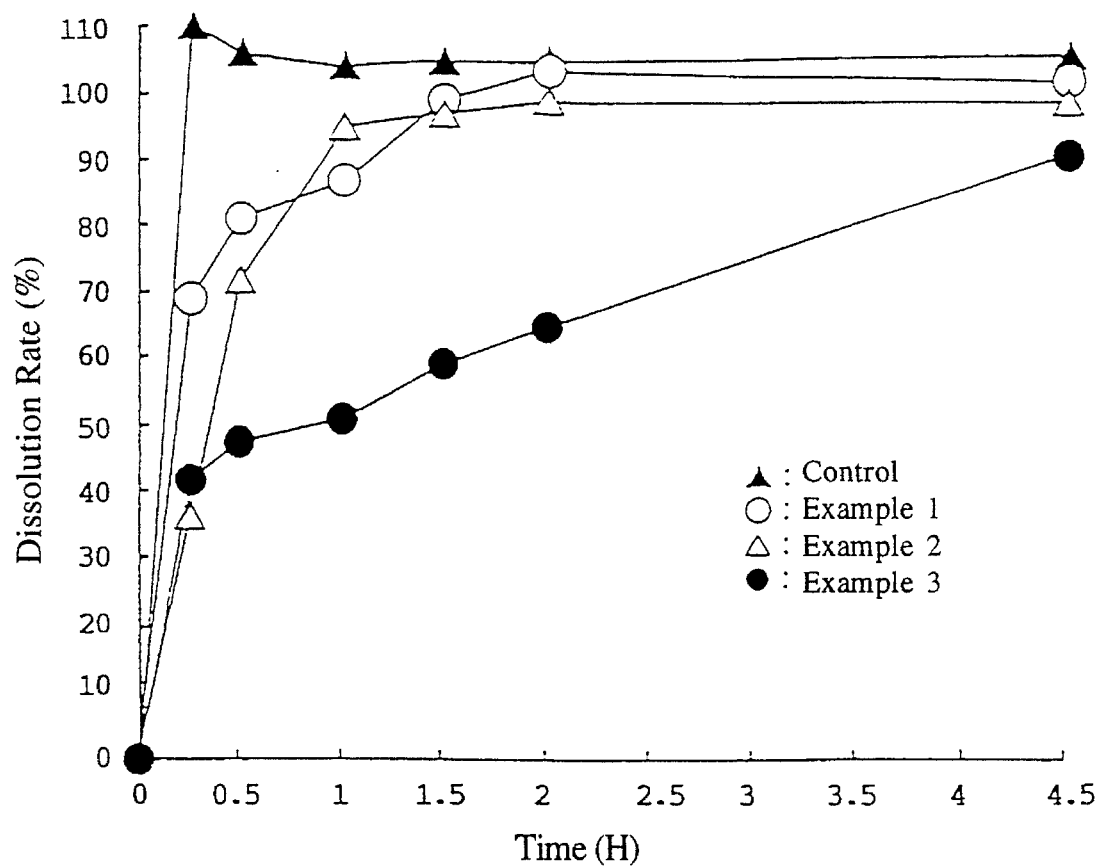
FIG. 1 shows the results of the dissolution test of the coated granules which are prepared in Examples 1 to 3, and the control granules.

The present invention is illustrated in more detail by Examples.

EXAMPLE 1

After gradually spraying as a binder an aqueous gelatin solution to spherical granules consisting of sugar crystals of 25–30 mesh and corn starch by rolling granulation, the spray powder consisting of phenylpropanolamine hydrochloride and corn starch was gradually sprayed thereto. These procedures were repeated, and the resulting granules were dried at 47° C. overnight, and screened to give spherical granules of a particle size of 20 to 30 mesh containing phenylpropanolamine hydrochloride.

To a centrifugal granulator (diameter: 36 cm), the above-obtained spherical granules (2 kg) containing phenylpropanolamine hydrochloride were charged. While rotating and flowing the granulator at 200 rpm, a melted mixture of paraffin (200 g) having a melting point of 87° C. which was melted at 150° C. was transported to the surfaces of these spherical granules at a rate of 5 ml/min. by a gear pump, and the thermally melted paraffin was mixed with a compressed air heated at 200° C. under a pressure of 0.3 kg/cm$^2$ within a two-fluid nozzle (Atomax® CN-200 type nozzle, manufactured by Seito Kyoritsu Syokai). The mixture of the thermally melted paraffin and the heated air was spray-coated onto the surfaces of the spherical granules containing phenylpropanolamine hydrochloride through the spray port while ejecting a heating gas from the other flow passage, wherein the two-fluid nozzle was set at a distance of 4 cm from the surfaces of the spherical granules containing phenylpropanolamine hydrochloride, and the temperature of the mixture of the thermally melted paraffin and the heating gas was controlled to be 95° C. at the surfaces of the spherical granules.

EXAMPLE 2

The spray-coating was carried out in the same manner as in Example 1 except that glycerin distearate (200 g) having a melting point of 58° C. was used instead of paraffin and melted at 120° C., and the compressed air was heated at 150° C. so that the temperature at the surfaces of the spherical granules containing phenylpropanolamine hydrochloride was 77° C.

EXAMPLE 3

Paraffin (400 g) having a melting point of 87° C. was spray-coated in the same manner as in Example 1.

The coated granules obtained in Examples 1 to 3 were tested in accordance with the dissolution test No. I method of Japanese Pharmacopeia, 12th-Edition (as a tested solution, purified water was used) in terms of the dissolution pattern of phenylpropanolamine hydrochloride, wherein the spherical uncoated granules containing phenylpropanolamine hydrochloride as used in the above Examples were used as a control. The results are shown in FIG. 1.

Industrial Applicability

As described above, according to the present coating method, which comprises spray-coating the surfaces of solid particles kept flowing with a thermally melted wax by using a two-fluid nozzle wherein the thermally melted wax and a heating gas are mixed and the resultant mixture is ejected from one flow passage and simultaneously the heating gas is ejected from the other flow passage, the desired sustained release preparations and preparations for masking materials of unpleasant and bitter tastes can be simply and easily prepared without problems of the conventional coating methods, i.e. without necessity of the use of toxic organic solvents, the complicated operations for pulverizing a wax and for thermally melting the wax powder deposited on solid particles, moreover, without occurrence of clogging of the nozzle, powdering of melted wax and forming of agglomerated solid particles.

We claim:

1. A coating method for spray-coating the surfaces of solid particles with a thermally melted wax, which comprises ejecting a mixture of a thermally melted wax and a heating gas from one of the flow passages of a two-fluid nozzle and, simultaneously, ejecting heating gas from the other flow passage of said two-fluid nozzle, the diameter of spray ports of said two-fluid nozzle being in the range of 1.5 to 5.8 mm, and said two-fluid nozzle having no needle valve.

2. The method according to claim 1, wherein said wax is one of the following or mixtures thereof:
   a) a higher alcohol selected from the group consisting of cetyl alcohol, stearyl alcohol and myristryl alcohol;
   b) a higher fatty acid selected from the group consisting of myristic acid, palmitic acid, stearic acid and behenic acid;
   c) a higher fatty acid glycerin ester selected from the group consisting of monoglyceride, diglyceride, triglyceride and polyglyceride;
   d) a higher hydrocarbon selected from the group consisting of paraffin, ceresin, and microcrystalline wax; or
   e) a fat, oil or wax which is solid at room temperature.

3. The method according to claim 2, wherein said oil is a member selected from the group consisting of hydrogenated soybean oil, hydrogenated castor oil, Japan wax and hydrogenated beef tallow, and said wax is a member selected from the group consisting of carnauba wax, candelilla wax and bees wax.

4. The method according to claim 1, wherein the temperature of the thermally melted wax and the heating gas are controlled so that the temperature thereof at the surfaces of the solid particles is 1° to 100° C. higher than a melting point of said wax.

5. The method according to claim 1, wherein the pressure of the heating gas is in the range of 0.05 to 10 kg/cm$^2$.

6. The method according to claim 1, wherein the solid particles are kept flowing by using a fluidized bed granulator, a centrifugal granulator, a conventional coating pan, a side vented coating pan, a vacuum coating pan, a high-shear mixer, or a combination of these apparatuses.

7. The method according to claim 4, wherein said temperature is controlled to 5° to 70° C. higher than the melting point of said wax.

8. The method according to claim 1, wherein said wax is heated to a temperature of 1° to 50° C. higher than the melting point of said wax and said gas is heated to 100° to 800° C.

9. The method according to claim 1, wherein said one of the flow passages is from 1 to 30 cm from the surfaces of said solid particles.

* * * * *